United States Patent [19]
Griffiths et al.

[11] Patent Number: 5,503,807
[45] Date of Patent: Apr. 2, 1996

[54] GAS ACTIVATION

[75] Inventors: Christopher N. Griffiths, Abingdon; David Raybone, Stow on the Wold; Keith H. Bayliss, Bridgnorth; John Stedman, Abingdon, all of United Kingdom

[73] Assignee: United Kingdom Atomic Energy Authority, Didcot, United Kingdom

[21] Appl. No.: 373,249

[22] PCT Filed: Jan. 27, 1994

[86] PCT No.: PCT/GB94/00158

§ 371 Date: Jan. 19, 1995

§ 102(e) Date: Jan. 19, 1995

[87] PCT Pub. No.: WO94/17835

PCT Pub. Date: Aug. 18, 1994

[30] Foreign Application Priority Data

Feb. 2, 1993 [GB] United Kingdom .................. 9301984
May 28, 1993 [GB] United Kingdom .................. 9311060

[51] Int. Cl.⁶ .................................................. B01J 19/12
[52] U.S. Cl. ................ 422/186.04; 422/186.21; 422/186.22; 422/186.29; 422/906; 422/907
[58] Field of Search ............... 422/186, 186.04, 422/186.21, 186.22, 186.29, 906, 907

[56] References Cited

U.S. PATENT DOCUMENTS

| | | |
|---|---|---|
| 4,348,357 | 9/1982 | Bithell . |
| 5,332,551 | 7/1994 | Koontz ..................................... 422/129 |
| 5,378,436 | 1/1995 | Endoh et al. ............................ 422/186 |
| 5,397,444 | 3/1995 | Zimer et al. .......................... 204/157.3 |
| 5,413,759 | 5/1995 | Campbell et al. ......................... 422/23 |
| 5,427,747 | 6/1995 | Kong et al. .............................. 422/186 |
| 5,437,844 | 8/1995 | Bonner .................................... 422/186 |

FOREIGN PATENT DOCUMENTS

| | | |
|---|---|---|
| 0387022 | 9/1990 | European Pat. Off. . |
| 1416723 | 12/1975 | United Kingdom . |
| 2253144 | 9/1992 | United Kingdom . |
| WO90/07466 | 7/1990 | WIPO . |

Primary Examiner—Ngoclan Mai
Assistant Examiner—Daniel Jenkins
Attorney, Agent, or Firm—William R. Hinds

[57] ABSTRACT

An apparatus for producing chemically active species by passing a precursor gaseous medium through a plasma at pressures of at least 50 millibars is described.

9 Claims, 3 Drawing Sheets

GAS ACTIVATION

The present invention relates to the generation of chemically active species, and more specifically, to the generation of such species for use in sterilisation processes.

The use of plasma-generated active gaseous species for sterilisation purposes is well-known. For example, such processes are described in our co-pending published patent application GB 2,253,144A (PCT application No. WO92/15336), U.S. Pat. Nos. 3,383,163; 3,851,436; 3,948,601; 4,207,286; 4,321,232; 4,348,357; 4,643,876; Japanese Application Disclosure numbers 103460/83; 162276/83; European patent application number 387022A, and others.

However, conventionally, the plasma is at a gas pressure well below atmospheric, typically in the range 1–10 torr. Such relatively low gas pressures place a limit on the amount of active species which can be generated and hence determine also the length of time required for the sterilisation of an object. Another disadvantage of the prior art systems is that their use involves relatively large scale vacuum systems with all the expense and operating procedures attached thereto.

It is an object of the present invention to provide an apparatus and method for producing active gaseous species at pressures substantially higher than hitherto.

According to the present invention there is provided an apparatus for generating chemically active gaseous species and exposing a substance to the chemically active gaseous species, comprising an activation chamber, means for generating an electric field within the activation chamber, a pair of electric field enhancing electrodes positioned within the activation chamber whereby a localised electric field sufficient to generate the chemically active species can be established, means for directing a gaseous medium adapted to provide the chemically active species through the region of maximum electric field in the proximity of the electric field enhancing electrodes, means for extracting the chemically active gaseous species from the activation chamber and a reaction vessel adapted to receive a substance to be exposed to the chemically active gaseous species.

In a preferred embodiment of the invention, the field enhancing electrodes consist of a pair of co-axial, opposed projections, at least one of which has an axial hole through which the chemically activated species can be withdrawn from the activation chamber, thereby to cause the gaseous medium to be directed into the region of maximum electric field between the field enhancing electrodes.

Also according to the invention there is provided a method of generating chemically active gaseous species, including the operations of establishing a high frequency alternating electric field in an activating chamber, shaping the electric field to provide a localised region of enhanced electric field such as to be capable of generating an electric discharge in a gaseous medium at a pressure of at least fifty millibars, admitting to the activation chamber at a pressure of at least fifty millibars a gaseous medium, the gaseous medium being adapted to provide the chemically active species under the influence of an electric discharge excited by the localised enhanced electric field, directing the gaseous medium through the localised region of enhanced electric field and extracting the chemically active species from the activation chamber, and admitting the chemically active species to a reaction chamber.

The chemically active species may be in the form of stable molecular species such as ozone or hydrogen peroxide, ions, free radicals, or electronically or vibrationally excited atomic or molecular species.

If the chemically active species are to be used for the sterilisation of objects such as surgical instruments or other objects which include degradable materials in their construction, then free radicals or stable chemically active molecular species are preferred. If the chemically active species are to be used to promote reactions such as polymerisation, then free radicals or vibrationally excited molecules are the preferred chemically active species.

Specific chemically active gaseous species which can be generated by means of the invention are ozone from oxygen gas or hydrogen peroxide from mixtures of oxygen, water vapour, nitrogen and hydrogen.

The invention will now be described, by way of example, with reference to the accompanying drawings in which,

DESCRIPTION OF A PREFERRED EMBODIMENT

Figure 1:
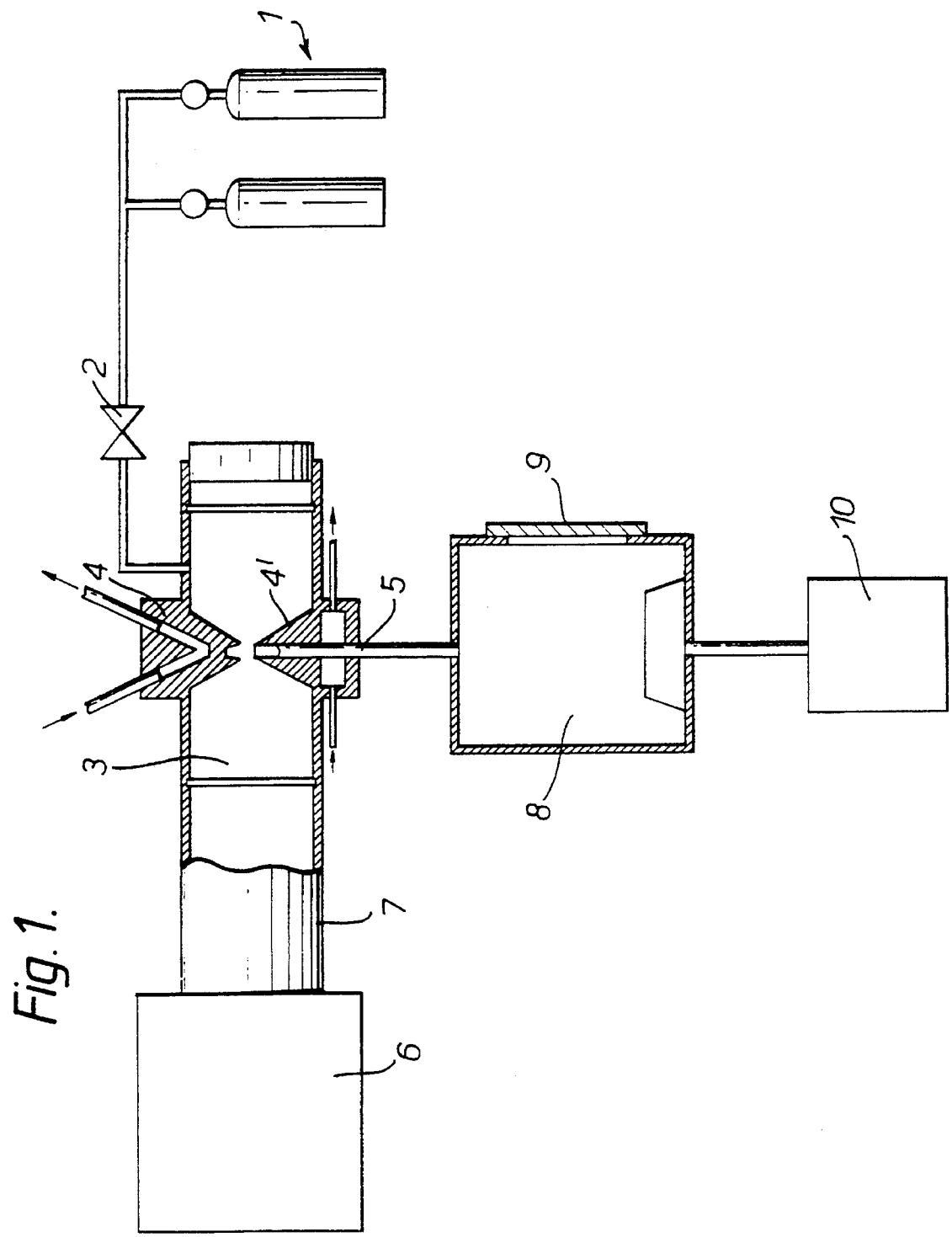
FIG. 1 is a schematic representation of an embodiment of the invention.

Referring to FIG. 1, there is shown schematically an apparatus embodying the invention for use in the sterilisation of objects. The apparatus consists of a source 1 of a gaseous medium from which chemically active gaseous species are to be generated, which may be a single gas, or a mixture of gases, a metering valve 2; and an activation chamber 3 containing a pair of electric field enhancing electrodes 4, one of which, 4', has an axial passage 5 through which the gaseous medium and chemically active species are withdrawn. Microwave radiation from a microwave generator 6 is applied to the activation chamber 3 by means of a suitable waveguide system 7. The chemically activated species from the activation chamber 3 are supplied to a sterilisation chamber 8 in which objects to be sterilised can be placed through a port 9. A pumping system 10 is arranged to extract spent gaseous medium from the sterilisation chamber 8. The electrode 4' is arranged to be water cooled, which also has the effect of cooling the gaseous medium as it leaves the activation chamber 3.

Figure 2:
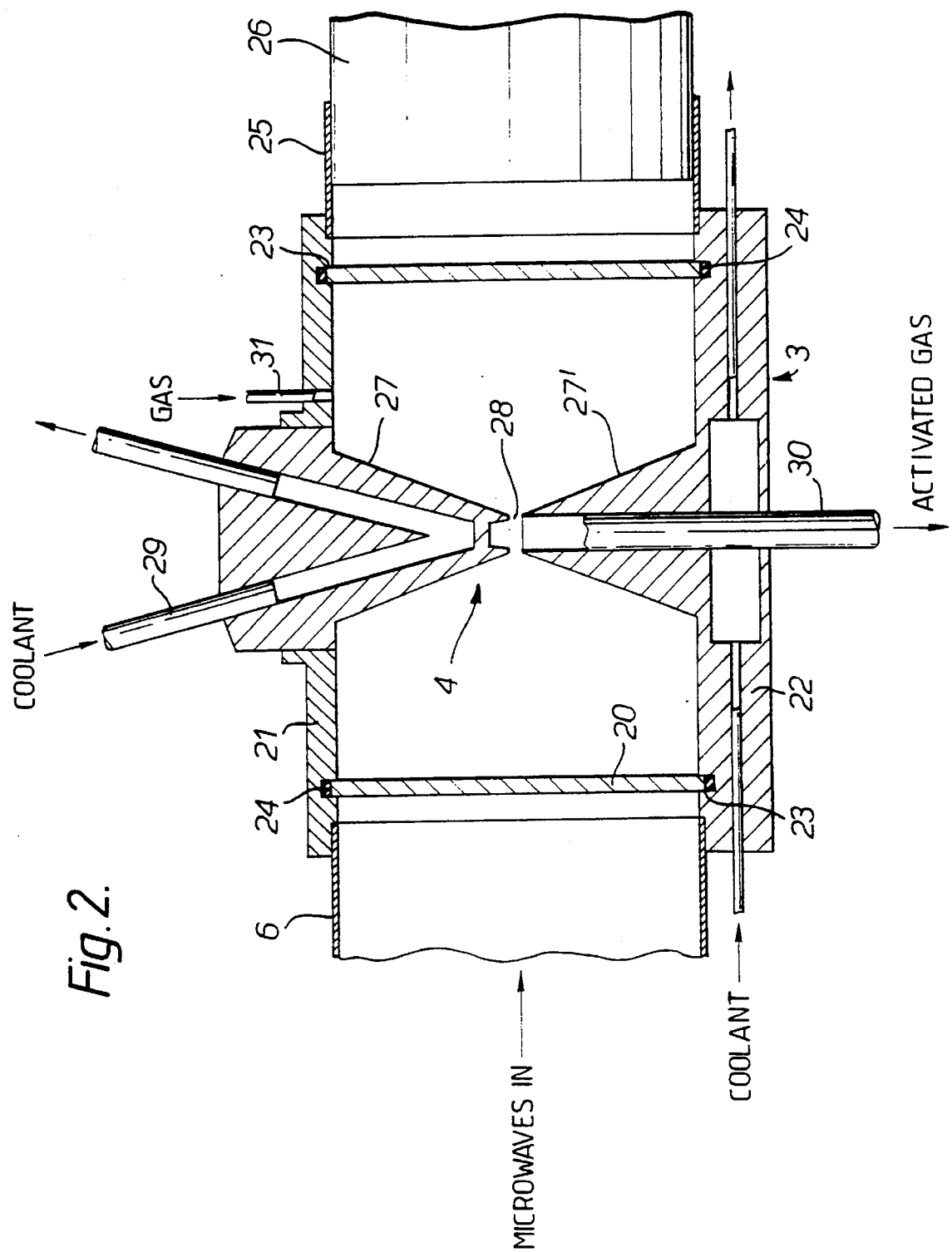
FIG. 2 shows in more detail an activation chamber included in the embodiment of FIG. 1.

Referring to FIG. 2 which shows the activation chamber 3 in more detail, the activation chamber 3 consists of a glass cylinder 20 and two end-pieces 21 and 22, respectively, which are made of stainless steel. The glass cylinder 20 fits into an annular groove 23 which is machined in each of the end-pieces 21 and 22. The activation chamber 3 is made gas-tight by means of O-ring seals 24. The end-pieces 21 and 22 are adapted to form part of the waveguide system 7 by means of which sufficient electrical energy is supplied to the activation chamber 3 to create a plasma in the gaseous medium within it. The waveguide 7 terminates in a stub 25 which includes a short-circuit 26 which can be fixed, or capable of sliding within the stub 25 for tuning purposes. The pair of electrodes 4 is formed by two conical projections 27 and 27' which form part of the end-pieces 21 and 22, respectively. The electrode 27 is made to be adjustable so that the gap 28 between the electrodes 27 and 27' can be altered to suit the operating conditions within the activation chamber 3. For most purposes, a gap of between 0.1 and 0.3 mm has been found to be satisfactory. The electrode 27 has a channel 29 formed in it through which a coolant can be circulated. The end-piece 22 is made hollow for the same purpose. The electrode 27, which is integral with the end-piece 22, has an axial passageway 30 formed in it by means of which the chemically active species and other constituents of the gaseous medium are withdrawn from the activation chamber 3. The gaseous medium is supplied to the activation chamber 3 through an inlet port 31.

The tips of the electrodes 27 and 27' are annular in shape, which has a number of effects. Firstly, there is the normal enhancement of the electric field in the activation chamber 3 due to the sharp edges of the annular tips of the electrodes 27 and 27'. Secondly, in the geometry shown, there is considerable drop in the pressure of the gaseous medium in the activation chamber 3 as it flows through the small gap 28 between the electrodes 27 and 27'. This not only means that it is easier to excite the gaseous medium to the plasma state in the vicinity of the tips of the electrodes 27 and 27' rather than elsewhere in the excitation chamber 3 where the gas pressure is higher, but the radial pressure drop across the activation chamber 3 confines the plasma to the vicinity of the gap 28 between the electrodes 27 and 27'. Also, the gaseous medium on its passage through the gap 28 between the electrodes 27 and 27' passes through the region of maximum electric field at right angles to the electric field, thus maximising the efficiency of the excitation of the gaseous medium to the plasma state, so reducing the electrical power required to generate the plasma. Furthermore, because the electric field distribution within the activation chamber 3 when it is operating does not differ greatly from that which exists when no plasma is present, the activation chamber 3 can be made to be self-starting. The operating environment of the tips of the electrodes 27 and 27' is very aggressive. The lifetime of the tips of the electrodes 27 and 27' can be extended by making them in the form of inserts made from a refractory or ceramic coated metal.

If desired, the electric field between the electrodes 27 and 27' can be further enhanced with respect to that in the remainder of the activation chamber 3 by applying a potential difference between the electrodes 27 and 27'. For this to be done, one of the electrodes 27 and 27' would have to be electrically isolated from its associated end-piece 21 or 22. Conveniently, this could be done by inserting a threaded insulating sleeve between the adjustable electrode 27 and its associated end-piece 21.

The net result is that plasmas can be generated economically at higher nominal pressures than hitherto and so higher gas pressures of chemically active species can be produced. For example oxygen or water vapour can be excited to form ozone, or hydrogen peroxide, respectively at pressures of up to an atmosphere, or even higher. Both these gases have bactericidal properties and are used for sterilisation purposes. The invention also can be used to form free radicals from chemical groups such as vinyl, phenyl, ethyl, styrene, methyl methacrylate, acrylonitrile and tetrafluoroethylene for use in polymerisation processes.

In one process for generating ozone, oxygen at a pressure of 500 mbar was passed through the activation chamber 3 at a flow rate of about 1 sl/min. 300 watts of microwave power at a frequency of 2.45 GHz were applied to the activation chamber 3 and ozone was produced in the resulting plasma which was formed in the region of the gap 28 between the field enhancing electrodes (27, 27').

In another process, a mixture of oxygen, nitrogen and water vapour was passed through the activation chamber 3 under the same conditions as before. As a result, hydrogen peroxide was formed.

If desired, the feed gas can be a mixture of the gas which is to provide the activated species and a carrier gas such as argon, helium or nitrogen. In the case of nitrogen, this gas also can be excited to a chemically active state.

The plasma formed in the activation chamber in which the chemically active species are created has a temperature of about 1000° C. For many purposes, particularly in connection with the sterilisation of objects which include plastics material, such temperatures are too high and temperatures of the order of 50° C. are required.

Figure 3:
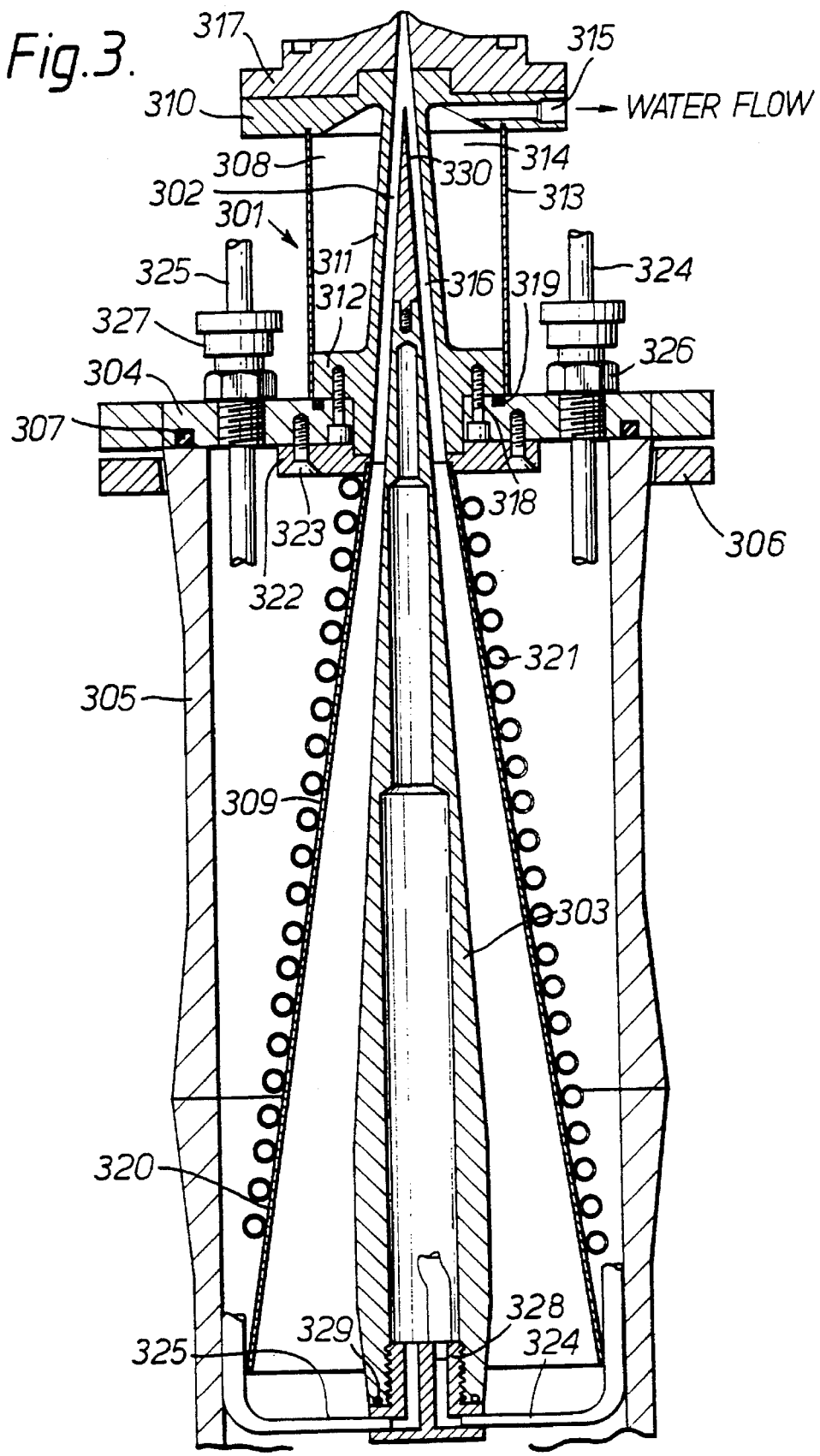
FIG. 3 shows a gas cooler which can be inserted between the activation chamber and the sterilisation chamber.

FIG. 3 shows a gas cooler which can be inserted between the activation chamber 3 and the sterilisation chamber 8 of the apparatus of FIG. 1.

Referring to FIG. 3, a cooler for an active gaseous medium derived from a plasma consists of a first, hollow, member 301, the inner surface 302 of which is conical in form. Positioned axially within the member 301 by means of two spiders, which are not shown, is a central member 303 which is conical in form also. The members 301 and 303 are mounted on a flange 304 which is clamped to a borosilicate glass tube 305 by means of a collar 306 and clamping bolts, which are not shown in the drawing. The junction between the flange 304 and the tube 305 is sealed by an O-ring 307. The glass tube 305 forms part of a sterilisation chamber the remainder of which is not shown in the drawing.

The member 301 has two sections, 308 and 309 respectively. The first section 308 of the member 301 is generally bobbin-shaped with an upper flange 310, a central shaft 311 and a lower flange 312. The shaft 311 of the first section 308 of the member 301 is surrounded by a cylindrical wall 313 which forms a water jacket 314. Water is circulated through the water jacket 314 via drillings 315 in the upper flange 310, only one of which is shown in the drawing. The shaft 311 of the first section 308 of the member 301 has a conical bore 16 the cone angle of which is four degrees. The outer surface of the shaft 311 of the first section 308 of the member 301 is taper-turned at the same angle so as to provide a constant wall thickness surrounding the bore 316. The upper flange 310 of the first section 308 of the member 301 is screwed into a member 317 which forms the electrode 27' of the activation chamber (3), the remainder of which is not shown, in which the plasma from which the active gas is derived is generated. The lower flange 312 of the first section 308 of the member 301 is attached to the flange 304 by means of set screws 318 and the junction between the flanges 304 and 312 is sealed by an O-ring 319.

The second section 309 of the member 301 consists of a conical trumpet 320 which is water cooled by means of a coil 321 on its outer surface and which has a flange 322 at its upper end by means of which it is attached to the flange 304 concentrically with the first section 308 of the member 301. The flange 322 is attached to the flange 304 by means of set screws 323. The internal diameters of the first and second sections 308 and 309, respectively, of the member 301 are identical so that there is no disturbance in the flow regime of the active gas as it passes from one to the other. The cone angle of the second section 309 of the member 301 is twenty degrees.

The central member 303 projects into the first section 308 of the member 301 as far as the upper flange 310 of the first section 308 of the member 301.

The major part of the member 303 is hollow and is cooled by means of water which is circulated through it via inlet and outlet pipes 324 and 325, respectively which pass through the flange 304 by means of gas-tight feedthroughs 326 and 327, respectively. The inlet and outlet pipes 324 and 325 also pass through an end-cap 328 which plugs the lower end of the member 303 and is sealed by an O-ring 329. As it is not practicable to water cool the tip 330 of the member 303 and the gas temperature at this point is about 1000° C., the tip 330 of the member 303 is made of a refractory material.

The cone angle of the member 303 is the same as that of the bore 316 of the section 308 of the member 301. Thus the annular passage between the inner surface 302 of the bore 316 of the shaft 311 of the first section 308 of the member 301 and the member 303 is of constant radial width, although its area increases at a rate which is proportional to the cone angle of the bore 311 and the member 303. This not only helps to cool the active gaseous medium by virtue of its expansion, but slows it down. During the passage of the active gaseous medium through the second section of the cooler 301, because of the difference between the cone angles of the member 303 and the conical portion 320 of the second section 309 of the member 301, the active gas is expanded much more rapidly than during its passage through the first section of the cooler 301.

The cone angles of the first and second stages of the cooler are controlled by the need to limit the expansion of the active gaseous medium to a value such that detachment of the boundary layer at the surfaces of the gas passage through the cooler does not occur. Also, if the expansion angle of the second section of the gas passage through the cooler is too large, then not only will flow separation occur, but also a pressure inversion can arise which will reduce the gas flow through the cooler, and hence its efficiency and that of the entire sterilisation apparatus of which it forms a part.

Suitable cone angles are from two to ten degrees for the first section 308 of the member 301 and twenty to forty degrees for the second section 309 of the member. The cone angle of the member 303 is constant and the same as that of the section 308 of the member 301.

Although it is most convenient to make the cooler of a metal such as copper (with the exception of the tip 330 of the member 303, which can be made of a refractory metal such as tungsten), this has the disadvantage that many metals tend to catalyse the deactivation of activated species in the active medium. Preferably, therefore, all those surfaces of the cooler which come into contact with the active medium have a thin layer of an inert ceramic material, such as alumina, deposited upon them.

In the arrangement described, simple conical sections are used. More control over the cooling and flow patterns of the gas can be achieved by using more sophisticated profiles for the surfaces which form the annular gas passage through the cooler. For example, the trumpet portion 320 of the second region 309 of the member 301 may be exponential in form.

We claim:

1. According to the present invention there is provided an apparatus for generating chemically active gaseous species and exposing a substance to the chemically active gaseous species, comprising an activation chamber, means for generating an electric field within the activation chamber, and a reaction vessel communicating with the activation chamber and adapted to receive a substance to be exposed to the chemically active gaseous species, wherein the activation chamber includes a pair of electric field enhancing electrodes (4, 4', 27, 27') positioned within the activation chamber (3) whereby a localised electric field sufficient to generate the chemically active species can be established, means for directing a gaseous medium adapted to provide the chemically active species through the region of maximum electric field (28) in the proximity of the electric field enhancing electrodes (4, 4', 27, 27'), means (5, 30, 10) for extracting the chemically active gaseous species from the activation chamber (3).

2. An apparatus according to claim 1 wherein the field enhancing electrodes (4, 4', 27, 27') consist of a pair of opposed projections (27, 27') at least one of which has an axial hole (30) communicating with the reaction vessel (8) so that the chemically activated gaseous species can be withdrawn from the activation chamber (3) via the region (28) of maximum electric field between the electrodes (4, 4', 27, 27') and admitted into the reaction vessel (8).

3. An apparatus according to claim 2 wherein there is included means (301) situated between the activation chamber (3) and the reaction vessel (8) for cooling the chemically activated gaseous species prior to their entry into the reaction chamber (8).

4. An apparatus according to claim 3 wherein the means (301) for cooling the chemically activated gaseous species comprises a chamber (305) having an axial inlet (316) for the gaseous medium, the inlet including a hollow member (301) having a first region (308) in which the cross-sectional area increases at a first pre-determined rate and a second region (309) in which the cross-sectional area increases at a second pre-determined rate greater than that of the first region.

5. An apparatus according to claim 4 wherein the inlet consists of a hollow first member (301) having a conical internal profile with a first region (308) having a first cone angle and a second region (309) having a second cone angle greater than that of the first region and there is provided means (313, 314, 315, 321) for cooling those surfaces of the first member (301) with which in use the gaseous medium to be cooled will come into contact.

6. An apparatus according to claim 5 wherein there is provided a second conical member mounted (303) co-axially within the first member (301), the second member (303) having the same cone angle as the first region (308) of the first member (301) and being such as to provide a first region of the inlet of constant radial width and a second region having an increasing radial width.

7. An apparatus according to claim 6 wherein at least the surface of the tip (330) of the second member (303) is made of a ceramic material.

8. An apparatus according to claim 4 wherein the inner surface (302) of the first member (301) is made of a ceramic material.

9. An apparatus according to any of claim 5 wherein the cone angle of the first region (308) of the hollow member (301) is about five degrees and the cone angle of the second region (309) of the working member (301) is between twenty and forty degrees.

* * * * *